(12) United States Patent
Ohnishi

(10) Patent No.: US 7,090,775 B2
(45) Date of Patent: Aug. 15, 2006

(54) SEPARATION AGENT FOR SEPARATING OPTICAL ISOMER AND METHOD FOR PREPARATION THEREOF

(75) Inventor: Atsushi Ohnishi, Ibaraki (JP)

(73) Assignee: Daicel Chemical Industries, Ltd., Osaka (JP)

( * ) Notice: Subject to any disclaimer, the term of this patent is extended or adjusted under 35 U.S.C. 154(b) by 8 days.

(21) Appl. No.: 10/480,398

(22) PCT Filed: Jul. 5, 2002

(86) PCT No.: PCT/JP02/06853

§ 371 (c)(1),
(2), (4) Date: Dec. 9, 2003

(87) PCT Pub. No.: WO03/004149

PCT Pub. Date: Jan. 16, 2003

(65) Prior Publication Data

US 2004/0188353 A1    Sep. 30, 2004

(30) Foreign Application Priority Data

Jul. 6, 2001  (JP)  .............................. 2001-206198

(51) Int. Cl.
*B01D 15/08* (2006.01)
(52) U.S. Cl. ................... 210/656; 210/635; 210/198.2; 210/502.1; 502/402; 502/404; 502/439
(58) Field of Classification Search ................ 210/656, 210/635, 198.2, 502.1; 502/404, 402, 439
See application file for complete search history.

(56) References Cited

U.S. PATENT DOCUMENTS

| | | | | |
|---|---|---|---|---|
| 4,213,860 A | * | 7/1980 | Tsibris | 210/656 |
| 4,539,399 A | * | 9/1985 | Armstrong | 536/103 |
| 4,619,970 A | | 10/1986 | Okamoto et al. | |
| 4,818,394 A | | 4/1989 | Okamoto et al. | |
| 4,912,205 A | | 3/1990 | Okamoto et al. | |
| 5,030,354 A | | 7/1991 | Miwa et al. | |
| 5,045,190 A | * | 9/1991 | Carbonell et al. | 210/198.2 |
| 5,202,433 A | * | 4/1993 | Okamoto et al. | 540/200 |
| RE34,457 E | | 11/1993 | Okamoto et al. | |
| 5,276,214 A | * | 1/1994 | Toda | 568/730 |
| 5,644,024 A | * | 7/1997 | Abrecht et al. | 530/317 |
| 5,734,043 A | | 3/1998 | Murakami et al. | |
| 5,868,938 A | | 2/1999 | Bomer et al. | |
| 5,965,026 A | * | 10/1999 | Oda et al. | 210/635 |
| 6,217,769 B1 | * | 4/2001 | Okamoto et al. | 210/635 |
| 6,783,672 B1 | * | 8/2004 | Tubbs et al. | 210/198.2 |
| 2004/0143024 A1 | * | 7/2004 | Yoshino et al. | 514/738 |

FOREIGN PATENT DOCUMENTS

| | | | |
|---|---|---|---|
| JP | 57-150432 | 9/1982 | |
| JP | 60-40952 | 3/1985 | |
| JP | 60-108751 | 6/1985 | |
| JP | 60-142930 | 7/1985 | |
| JP | 62-211552 | 9/1987 | |
| JP | 63-178101 | 7/1988 | |
| JP | 63-307829 | 12/1988 | |
| JP | 5-232098 | 9/1993 | |
| JP | 6-343857 | 12/1994 | |
| WO | WO 99/18052 | * 4/1999 | 210/198.2 |

OTHER PUBLICATIONS

PTO Translation No. 05-3256 of Japan Patent No. 06-343857, Apr. 2005.*
PTO Translation No. 05-3248 of Japan Patent No. 05-232098, Apr. 2005.*
"Polysaccharide Derivatives for Chromatographic Separation of Enantiomers", by Yoshio Okamoto et al, Angew. Chem. Int. Ed., 1998, 37, 1020-1043.
"Separation of chiral compounds", by Shigeo Makino, Pharm. Tech. Japan, vol. 12, 1996, 43-52.
"Uber die Anwendung von enzymanalog gebauten Polymeren zur Racemattrennung", by G. Wulff et al, Anger. Chem., 1972, 84, 364.

* cited by examiner

*Primary Examiner*—Ernest G. Therkorn
(74) *Attorney, Agent, or Firm*—Flynn, Thiel, Boutell & Tanis, P.C.

(57) ABSTRACT

A method of producing a novel separating agent for separating enantiomeric isomers, characterized by including: a step of supporting an optically active polymer compound and a compound having an asymmetric structure of a molecular weight of 1,000 or less on a carrier using a solvent; a step of removing the solvent; and a step of removing the compound having the asymmetric structure of the molecular weight of 1,000 or less by washing.

30 Claims, No Drawings

SEPARATION AGENT FOR SEPARATING OPTICAL ISOMER AND METHOD FOR PREPARATION THEREOF

REFERENCE TO RELATED APPLICATIONS

This application is a 371 of PCT/JP02/06853 filed Jul. 5, 2002.

TECHNICAL FIELD

The present invention relates to a novel separating agent for separating enantiomeric isomers, a method of producing the same, and a separation method for enantiometric isomers using the same, in particular, a separation method for enantiomeric isomers with chromatography. The present invention provides a separation technique of the enantiomeric isomers, which enable the optical resolution of chiral compounds with a high separation coefficient in analyses of medicines, foods, agricultural chemicals, fragrant materials, and the like.

BACKGROUND ART

Many organic compounds have enantiomeric isomers which have completely the same physical and chemical properties but differ in physiological activity. This is attributable to the following. In most cases, proteins or glucides per se constituting a living being are composed of only one of the enantiomeric isomers, and for this reason, a difference arising in the manner of acting on the other enantiomeric isomer results in a difference in physiological activity. In particular, in many cases, there are significant differences in medical properties and toxicity between the enantiomeric isomers of the pharmaceuticals, and this problem is recognized as a significant problem in the field of pharmaceuticals. The Ministry of Health, Labour and Welfare of Japan prescribes in the Guideline for the Production of Medicines that "in the case where the drug is a racemi form, it is desirable that studies on the dynamic behaviors of absorption, distribution, metabolism and excretion be made on each enantiomeric isomer".

Since the enantiomeric isomers have completely the same physical and chemical properties, for example, the physical properties such as a boiling point, a melting point or a solubility, as described above, they cannot be analyzed by ordinary separation means. For this reason, extensive investigations have been made on techniques for analyzing a wide variety of enantiomeric isomers in a simple manner and with a high precision. As a result, an optical resolution method by high performance liquid chromatography (HPLC), in particular, an optical resolution method using an enantiomeric isomer separation column for HPLC has been developed as an analyzing method that meets those requirements. The enantiomeric isomer separation column defined herein uses an asymmetry identifying agent itself or a chiral immobilizing phase having the asymmetry identifying agent supported on a suitable carrier.

As examples of the chiral immobilizing phase, optically active poly(triphenylmethyl methacrylate) (cf., JP-A 57-150432), cellulose and amylose derivatives (cf., JP-A 60-40952, JP-A 60-108751, JP-A 60-142930 and JP-A 63-178101), ovomucoid, which is a protein (JP-A 63-307829), and the like have been developed. It is known that, of the many chiral immobilizing phases for HPLC, a column for enantiomeric isomer separation having the cellulose or amylose derivatives supported on silica gel has a high asymmetry identification ability for a very wide variety of compounds (for example, Okamoto et al., Angew. Chem. Int. Ed., 1998, 37, 1020).

In the case of aiming at analyses such as an optical purity measurement, it has been desired that as many unidentified enantiomeric isomer compounds as possible can be separated by as few kinds as possible of enantiomeric isomer separation columns. As a result, the above-mentioned column for enantiomeric isomer separation having the cellulose or amylose derivatives supported on the silica gel has been accepted as practical separation media.

In recent years, studies on liquid preparative chromatography for optically active substances on an industrial scale in a combination of a chiral immobilizing phase for HPLC and a simulated moving bed method have been developed (Phrarm. Tech. Japan, 12, 43(1996). In such studies, not only analysis, but also preparative separation, namely, chromatographic separation as a production means, are noted.

For that purpose, in order to not only merely perform base line separation, but to improve the productivity of the preparative chromatography and decrease the production cost, it has been demanded to develop a chiral immobilizing phase that enables the further separation of a target compound for the limited, specified preparative separation, that is, has a value of separation coefficient $\alpha$ as high as possible.

On the other hand, a molecular imprinting method is known as a method of specifically identifying the specific target compound. The most popular method in general production methods for a molecular template is that the target compound (guest) and a monomer for performing non-conjugated-bond-type interaction therewith are reacted in a test tube using a crosslinking agent or the like for polymerization, thereby obtaining a polymer compound (host). Further, a method of obtaining a host by mixing the guest and a polymer and subjecting the polymer to a crosslinking reaction in an interaction state is known (for example, G. Wulff et al., Angew. Chem., 1972, 84, 364).

A filler for chromatography obtained by such molecular imprinting has a high identification ability for a guest. However, it is known that such a filler is extremely high in its degree of adsorption for a guest, and as a result, the corresponding elution peak shows a widely extended form. This is not satisfactory in terms of chromatography efficiency. Further, the polymer compound obtained by the molecular imprinting method cannot include a dissolution operation that may decompose a prepared template. For this reason, the polymer compound is prepared into the filler for chromatography by pulverization processing or the like. However, an operation such as classification is complicated, and a particle size is not uniform, resulting in a decrease in chromatography efficiency. For the above reason, the filler for chromatography obtained by the technique using the molecular imprinting method has not been yet put into practical use.

A purpose of the present invention is to provide a process for producing a novel separating agent for separating enantiomeric isomers to obtain a separating agent for separating enantiomeric isomers, which is greatly improved in separation efficiency for objective compounds for separation.

Another purpose of the present invention is to provide a separating agent for separating enantiomeric isomers, which has a greatly improved separation performance for a compound to be separated and can separate compounds that could not conventionally be separated.

Still another purpose of the present invention is to provide an immobilizing phase for chromatography or an immobilizing phase for continuous liquid preparative chromatography, using the separating agent for separating enantiomeric isomers, and a separation method for enantiomeric isomers using the separating agent for separating enantiomeric isomers.

DISCLOSURE OF THE INVENTION

The present inventors have found that a separation ability is greatly improved by improving a separating agent for separating enantiomeric isomers, in place of selective use of a general-purpose developing solvent conventionally used, specifically improving the separating agent for separating enantiomeric isomers using a compound having an asymmetric structure of a molecular weight of 1,000 or less, as a method of increasing the separation ability of the separating agent for separating enantiomeric isomers.

More specifically, according to the present invention, there is provided a method of producing a novel separating agent for separating enantiomeric isomers, characterized by including the addition of a compound having an asymmetric structure of a molecular weight of 1,000 or less in supporting an optically active polymer compound on a carrier.

Further, according to the present invention, there is provided a method of producing a novel separating agent for separating enantiomeric isomers, characterized by including: a step of supporting an optically active polymer compound and a compound having an asymmetric structure of a molecular weight of 1,000 or less on a carrier using a solvent; and a step of removing the solvent.

Further, according to the present invention, there is provided a method of producing a novel separating agent for separating enantiomeric isomers, characterized by including: a step of supporting an optically active polymer compound and a compound having an asymmetric structure of a molecular weight of 1,000 or less on a carrier using a solvent; a step of removing the solvent; and a step of removing the compound having the asymmetric structure of the molecular weight of 1,000 or less by washing.

Further, according to the present invention, there is provided a method of producing a novel separating agent for separating enantiomeric isomers, characterized by including: a step of supporting an optically active polymer compound on a carrier using a solvent; a step of additionally supporting a compound having an asymmetric structure of a molecular weight of 1,000 or less on the carrier; and a step of removing the solvent.

Further, according to the present invention, there is provided a method of producing a novel separating agent for separating enantiomeric isomers, characterized by including: a step of supporting an optically active polymer compound on a carrier using a solvent; a step of additionally supporting a compound having an asymmetric structure of a molecular weight of 1,000 or less on the carrier; a step of removing the solvent; and a step of removing the compound having the asymmetric structure of the molecular weight of 1,000 or less by washing.

Further, according to the present invention, there is provided a separating agent for separating enantiomeric isomers, including an optically active polymer compound supported on a carrier, from which a compound having an asymmetric structure of a molecular weight of 1,000 or less added as a production raw material and supported is removed.

Further, according to the present invention, there is provided an immobilizing phase for chromatography using the separating agent for separating enantiomeric isomers or an immobilizing phase for a continuous liquid preparative chromatography using the separating agent for separating enantiomeric isomers or a separation method for enantiomeric isomers using the separating agent for separating enantiomeric isomers.

BEST MODE FOR CARRYING OUT THE INVENTION

A method of producing a novel separating agent for separating enantiomeric isomers of the present invention is described.

The production method of the present invention includes a step of adding a compound having an asymmetric structure of a molecular weight of 1,000 or less in supporting an optically active polymer compound on a carrier, and a production method including the following steps can be exemplified as the production method including the above step.

Firstly, in a first step, an optically active polymer compound and a compound having an asymmetric structure of a molecular weight of 1,000 or less are supported on a carrier using a solvent. Here, in the present invention, the optically active polymer compound is directly supported on the carrier. However, the compound having the asymmetric structure of the molecular weight of 1,000 or less is not directly supported on the carrier, but is indirectly supported on the carrier by physically or chemically bonding it to the optically active polymer compound.

In this step, the following methods can be applied:

(1) a method of preparing a solvent solution of an optically active polymer compound and the compound having the asymmetric structure of the molecular weight of 1,000 or less, and bringing the solution and the carrier in contact with each other by a method of immersing the carrier in the solution, a method of applying the solution to the carrier, or the like, thereby supporting it on the carrier; and (2) a method of preparing the solvent solution of the optically active polymer compound, contact-supporting the solution on the carrier by a method of immersing the carrier in the solution, and dissolving the compound having the asymmetric structure of the molecular weight of 1,000 or less in the solution, or after preparation of the solvent solution, adding the solvent solution of the compound having the asymmetric structure of the molecular weight of 1,000 or less to the solution, thereby supporting it on the carrier.

The term "supporting" used herein means that an optically active polymer compound and a compound having an asymmetric structure of a molecular weight of 1,000 or less are fixed to the carrier. This fixation is performed by physical adsorption and/or chemical bonding between the optically active polymer compound and a compound having an asymmetric structure of a molecular weight of 1,000 or less, and a carrier.

The physical adsorption means that the compound is adsorbed on a surface of the carrier and/or inside fine pores of the carrier.

The chemical bonding includes bonding between a carrier and an optically active polymer compound, bonding between a part of the optically active polymer compound physically adsorbed on the carrier, bonding between remaining optically active polymer compound and the compound having the asymmetric structure of the molecular weight of 1,000 or less, and chemical bonding between the carrier and the optically active polymer compound by reaction with a crosslinking agent, reaction with a radical generator or light irradiation (irradiation with radiation such as γ-rays, or irradiation with electromagnetic waves such as microwaves).

When chemically bonding the carrier and the optically active polymer compound, it is desirable to perform chemical bonding before or after a step of removing the compound having the asymmetric structure of the molecular weight of 1,000 or less as a post-step.

Examples of the optically active polymer compound used in the present invention include polymers or copolymers of (meth)acrylates or (meth)acrylamides that do not have optically active substituents, (meth)acrylates or (meth)acrylamides having the optically active substituents, styrene, acetylene or the like, polysaccharides or their derivatives, peptides, and proteins.

Of those, the polymer compounds having the asymmetry identification ability for a compound to be separated are preferable. In particular, the polymers or copolymers of (meth)acrylates or (meth)acrylamides, polysaccharides and their derivatives, and proteins that are known to have the asymmetry identification ability are preferable, polymers or copolymers of (meth)acrylamides or (meth)acrylates, polysaccharides and their derivatives having optically active substituents at side chains are more preferable, and polysaccharide derivatives are most preferable.

Note that, the (meth)acrylates used in this specification mean acrylates and methacrylates, and the (meth)acrylamides used in this specification mean acrylamides and methacrylamides.

As a polysaccharide, any synthetic polysaccharide, any natural polysaccharide, and any modified natural polysaccharide may be used so long as they have an optical activity. Those which have a high regularity in the binding form are more desired.

There are exemplified β-1,4-glucan (cellulose), α-1,4-glucan (amylose, amylopectin), α-1,6-glucan (dextran), β-1,6-glucan (busturan), β-1,3-glucan (for example, curdlan, schizophyllan, etc.), α-1,3-glucan, β-1,2-glucan (Crown Gall polysaccharide), β-1,4-galactan, β-1,4-mannan, α-1,6-mannan, β-1,2-fructan (inulin), β-2,6-fructan (levan), β-1,4-xylan, β-1,3-xylan, β-1,4-chitosan, α-1,4-N-acetylchitosan (chitin), pullulan, agarose, alginic acid, and the like. Also, the polysaccharide includes starch containing amylose.

Among those, cellulose, amylose, β-1,4-xylan, β-1,4-chitosan, chitin, β-1,4-mannan, inulin, and curdlan, which are readily available as a polysaccharide having a high purity, are preferred. Cellulose and amylose are particularly preferred.

These polysaccharides have a number-average degree of polymerization (an average number of pyranose rings or furanose rings contained in one molecule) of at least 5, preferably at least 10, or preferably 1,000 or less in view of ease of handling, though there is no particular limitation in the upper limit thereof.

The polysaccharide derivative is a compound combined with a compound having a functional group reactive with part or all of the hydroxyl groups of the polysaccharide through an ester bond, an urethane bond or an ether bond.

The compound having a functional group capable of reacting with a hydroxyl group can be any compound so long as it is a compound having leaving groups such as substituted or unsubstituted aromatic, aliphatic or alicyclic carboxylic acids, acid halides, acid anhydrides, carboxylic acid derivatives such as acid ester, substituted or unsubstituted aromatic, aliphatic or alicyclic isocyanic acid derivatives, alcohols, and other compounds. The compound may have or may not have optically active groups.

Preferable polysaccharide derivatives are polysaccharide ester derivatives and carbamate derivatives, and polysaccharide ester derivatives and carbamate derivatives having 0.1 or more, per glucose unit, of ester bond or urethane bond are particularly preferable.

The amount of the optically active polymer compound used is such an amount that the amount of the compound supported on a carrier with respect to a carrier mass preferably corresponds to 1 to 100 mass %, more preferably 5 to 60 mass %, and most preferably 10 to 40 mass %.

The compound having the asymmetric structure of the molecular weight of 1,000 or less used in the present invention includes the following (I) and (II).

(I) A compound to be separated in the case of being used as a separating agent for separating enantiomeric isomers, or its similarly structured compound. The "similarly structured compound" used herein is a compound in which a functional group is similar to that of the compound to be separated, the number of methylene chains increases or decreases, the number of substituents increases or decreases, a position of the functional group differs, and a kind of functional group differs from the compound to be separated and which accordingly has such a structure that a molecular size is, for example, larger by about 1 to 5 carbon atoms or smaller by about 1 to 5 carbon atoms. Examples of the similarly structured compound, with respect to 1-phenyl-2-propanol, include 1-phenylethanol, 2-phenyl-2-propanol, 1-phenyl-2-butanol, 2-phenyl-2-butanol, 3-phenyl-2-butanol, 1-substituted phenyl-2-propanol, 1-(1-naphthyl)-2-propanol, 1-(2-pyridyl)-2-propanol, and 1-cyclohexyl-2-propanol. Examples of the similarly structured compound, with respect to 1-(1-naphthyl)-ethanol, include 1-(9-anthryl)-ethanol.

Besides, the "similarly structured compound" includes compounds in which environmental conditions around the asymmetric carbon are similar.

(II) A compound to be separated in the case of being used as a separating agent for separating enantiomeric isomers, or a compound other than a similarly structured compound thereof, preferably a compound having a cyclic structure of a molecular weight of 40 to 1,000, preferably 60 to 600.

Preferable compounds (I) and (II) are compounds having a polar functional group such as a heteroatomic group, e.g., a hydroxyl group, a carbonyl group, an amino group or a carboxyl group, compounds having a functional group related to π-electron interaction, such as a benzene ring, racemi form (±), and optically active substance (+) or (−) are preferable.

The compound (I) has a molecular weight of 40 or more, preferably 60 to 1,000, and more preferably 100 to 500.

The compound having the asymmetric structure of the molecular weight of 1,000 or less is used in an amount of preferably 0.01 to 1,000 mass %, more preferably 0.01 to 200 mass %, and most preferably 0.1 to 30 mass %, based on the mass of the optically active polymer compound supported on a carrier.

The carrier used in the present invention includes organic porous carriers and inorganic porous carriers. The inorganic porous carriers are preferable. Suitable examples of the organic porous carrier include polymer substances including polystyrenes, polyacrylamides, polyacrylates, or the like. Suitable examples of the inorganic porous carrier include silica, alumina, magnesia, glass, kaolin, titanium oxide, silicates and hydroxyapatites.

Silica gel is a particularly preferable carrier. The silica gel has a particle diameter of 0.1 μm to 10 mm, preferably 1 μm to 300 μm, and most preferably 1 to 100 μm, and an average pore diameter of 10 Å to 100 μm, and preferably 50 to 50,000 Å. Surface treatment may be applied to the surface of silica gel in order to eliminate effects of residual silanol, but there is no problem even though the surface treatment is not applied to the surface.

The solvent used in the present invention may be any generally-used organic solvent so long as it can dissolve the optically active polymer compound and the compound having the asymmetric structure of the molecular weight of 1,000 or less.

Examples of the solvent include ketone solvents such as acetone, ethyl methyl ketone or acetophenone; ester solvents such as ethyl acetate, methyl acetate, propyl acetate, methyl propionate or phenyl acetate; ether solvents such as tetrahydrofuran, 1,4-dioxane, diethyl ether, tert-butyl methyl ether or anisole; amide solvents such as N,N-dimethylformamide; imide solvents such as N,N-dimethylimidazolidinone; halogen solvents such as chloroform, methylene chloride, carbon tetrachloride, 1,2-dichloroethane or pentafluoroethanol; hydrocarbon solvents such as pentane, petroleum ether, hexane, heptane, octane, benzene, toluene, xylene or mesitylene; alcohol solvents such as methanol, ethanol, propanol or butanol; acid solvents such as acetic acid, trifluoroacetic acid or formic acid; phenol solvent such as phenol or catechol; and amine solvents such as diethylamine, triethylamine, pyridine or aniline.

In preparing the optically active polymer compound and the compound having the asymmetric structure of the molecular weight of 1,000 or less using such a solvent, a solution concentration is not particularly limited, and is determined considering ease of contact-supporting treatment with the carrier, and removal treatment of a solvent in a post-step.

A solvent used to support the optically active polymer compound and the compound having the asymmetric structure of the molecular weight of 1,000 or less on the carrier is removed in the next step.

In the solvent removal treatment in this step, the optically active polymer compound is still directly supported on the carrier, and the compound having the asymmetric structure of the molecular weight of 1,000 or less maintains the state of being indirectly supported on the carrier.

In the next step, the optically active polymer compound and the compound having the asymmetric structure of the molecular weight of 1,000 or less are washed in the state where they are supported on the carrier, thereby removing the compound having the asymmetric structure of the molecular weight of 1,000 or less.

The washing step can adopt, for example, a method of refluxing under any temperature of 0° C. to a reflux temperature using acetonitrile, alcohol, hexane, a mixed solvent of hexane and alcohol, or the like.

The amount of solvent used in the case of adopting the reflux method is about 3 to 50 times the mass of the carrier having supported thereon the optically active polymer compound and the compound having the asymmetric structure of the molecular weight of 1,000 or less.

A residual amount of the compound having the asymmetric structure of the molecular weight of 1,000 or less after the washing treatment of this step is, when finally formed into a separating agent for separating enantiomeric isomers, preferably 10 mass % or less, more preferably 2 mass % or less, and most preferably 0.5 mass % or less, in the separating agent. The compound having the asymmetric structure of the molecular weight of 1,000 or less may be contained as an impurity if the content is less than the above value.

Further, the compound having the asymmetric structure of the molecular weight of 1,000 or less after the washing treatment of this step can be substantially removed as well.

A separating agent for separating enantiomeric isomers obtained according to the producing method of the present invention includes an optically active polymer compound supported on a carrier, further, from which a compound having an asymmetric structure of a molecular weight of 1,000 or less added as a production raw material and supported is removed.

In the separating agent for separating enantiomeric isomers obtained according to the producing method of the present invention, the compound having the asymmetric structure of the molecular weight of 1,000 or less is the compound of the item (I) or (II), and when the enantiomeric isomers are separated using the separating agent for separating the enantiomeric isomers, a separation performance based on a separation coefficient ($\alpha$) obtained by the following equation:

separation coefficient ($\alpha$)=(holding coefficient of enantiomer held relatively strongly)/(holding coefficient of enantiomer held relatively weakly)

holding coefficient ($k'$)=[(holding time of the enantiomer)−(dead time)]/(dead time), where, the dead time is set as elution time of tri-tert-butylbenzene, is desirably shown by the following equation (A) or equation (B):

$$\alpha_1/\alpha_2 \geq 1.05 \text{ (provided } \alpha_2=1.00) \quad (A)$$

$$\alpha_1/\alpha_2 \geq 1.05 \text{ (provided } \alpha_2>1.00) \quad (B)$$

where $\alpha_1$: a separation coefficient of the separating agent for separating the enantiomeric isomers obtained by adding the compound having the asymmetric structure of the molecular weight of 1,000 or less in a production step, and $\alpha_2$: a separation coefficient of the separating agent for separating the enantiomeric isomers obtained without adding the compound having the asymmetric structure of the molecular weight of 1,000 or less in the production step, in which $\alpha_2=1.00$ means that the enantiomeric isomers are not separated al all, and $\alpha_2>1.00$ means that the enantiomeric isomers are separated.

The equation (A) shows $\alpha_2=1.00$, that is, the fact that separation performance of a compound that involves absolutely no separation in the case of using a separating agent for separating enantiomeric isomers obtained without adding a compound having an asymmetric structure of a molecular weight of 1,000 or less in the production step is improved by 5% or more in the case of using the separating agent for separating enantiomeric isomers of the present invention.

The equation (B) shows $\alpha_2>1.00$, that is, the fact that separation performance in the case of using a separating agent for separating enantiomeric isomers obtained without adding a compound having an asymmetric structure of a molecular weight of 1,000 or less in the production step is improved by 5% or more in the case of using the separating agent for separating enantiomeric isomers of the present invention. In the present invention, the separation performance defined by the equation (B) is improved by preferably 10% or more, more preferably 15% or more, and most preferably 20% or more.

The separating agent for separating enantiomeric isomers of the present invention can be used as an immobilizing phase for chromatography such as gas chromatography, liquid chromatography, thin layer chromatography, supercritical chromatography or capillary electrophoresis. In particular, it is preferably used as the chiral immobilizing phase for liquid chromatography. It can also be suitably used as an immobilizing phase for continuous liquid preparative chromatography represented by a simulated moving bed chromatography. The enantiomeric isomers can be separated with good efficiency using such a separating agent of the present invention.

INDUSTRIAL APPLICABILITY

The present invention can greatly improve the separation performance of a separating agent for separating enantiomeric isomers, and particularly, such a separating agent is suitable as an immobilizing phase for chromatography and an immobilizing phase for continuous liquid preparative chromatography.

EXAMPLES

The present invention is described in detail based on examples, but the present invention is not limited to those examples.

A representation of the compounds described hereinafter is based on any compound selected from the following compounds 1 to 16. With respect to a compound having an asymmetric structure of a molecular weight of 1,000 or less and a compound to be separated, representation of steric configuration (S,R), optical activity (D,L) and racemi form is combined with each compound number. For example, when the compound 1 has an S configuration, it is expressed as S-1, and when the compound 1 is a racemi form, it is expressed as racemi form-1.

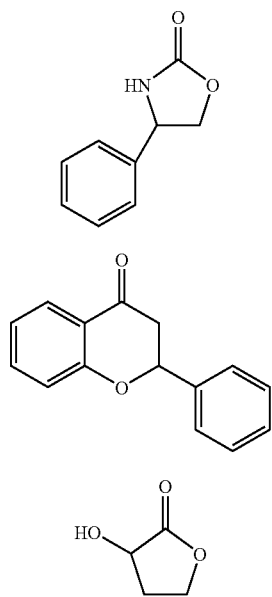

Compound 1

Compound 2

Compound 3

-continued

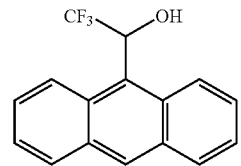

Compound 4

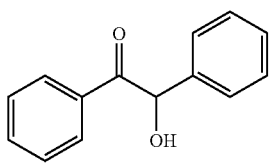

Compound 5

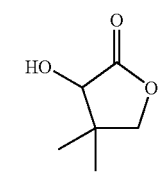

Compound 6

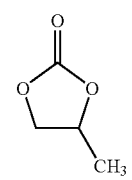

Compound 7

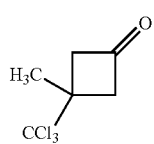

Compound 8

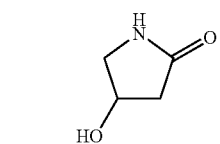

Compound 9

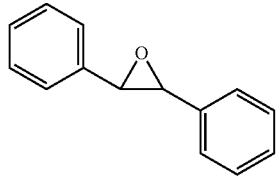

Compound 10

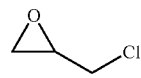

Compound 11

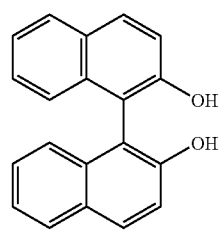

Compound 12

-continued

Compound 13

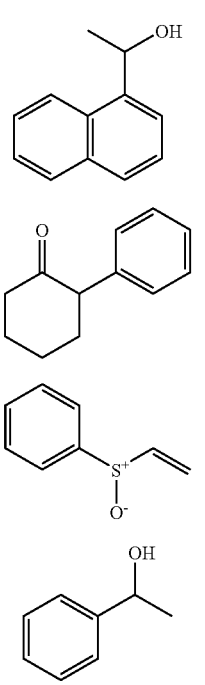

Compound 14

Compound 15

Compound 16

Example 1

(1) Surface Treatment of Carrier (Silica Gel)

Porous silica gel (particle diameter: 7 μm, micropore: 1,000 Å) was reacted with 3-aminopropyltriethoxysilane using any conventional method to perform aminopropylsilane treatment.

(2) Synthesis of Optically Active Polymer Compound 15.0 g of lithium chloride in an absolute dry state was dissolved in 150 ml of N,N-dimethylacetamide (DMAc) to prepare a DMAc/LiCl solution.

In a nitrogen atmosphere, 150 ml of the above DMAc/LiCl solution and 150 ml of pyridine were added to 10.0 g of cellulose, and the resulting mixture was immersed in an oil bath at 100° C. and stirred for 24 hours. Thereafter, 50 g of 4-methylbenzoyl chloride was added to the mixture to conduct a reaction at 100° C. for 16 hours.

The reaction liquid was added dropwise to 2 L of methanol, followed by reprecipitation and centrifugal separation, thereby obtaining the objective cellulose tris(4-methylbenzoate) represented by the following formula.

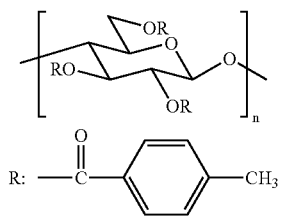

(3) Preparation of Separating Agent for Separating Enantiomeric Isomers 0.8 g of cellulose tris(4-methylbenzoate) obtained in (2) above and 506.0 mg of a compound (S-1) (2-fold molar equivalent to glucose unit of cellulose tris(4-methylbenzoate)) were dissolved in methylene chloride to prepare a dope. This dope was applied to 3.2 g of silica gel obtained in (1) above. After the application, methylene chloride was distilled off to obtain the objective separating agent for separating enantiomeric isomers. This separating agent was added to a mixed solvent of n-hexane/2-propanol, and the resulting mixture was well stirred, and filtered. The filtrate was condensed to recover 495.6 mg of (S-1).

(4) Preparation of Packed Column for HPLC

A stainless steel-made column having a length of 25 cm and an inner diameter of 0.46 cm was packed with the separating agent for separating enantiomeric isomers obtained in (3) above by a slurry packing method using a mixed solvent of n-hexane/2-propanol to obtain a separation column for enantiomeric isomers.

S-1 residual amount in the separating agent for separating enantiomeric isomers: 506.0−495.6=10.4 mg Elution rate of S-1: 495.6/506.0×100=97.9%

S-1 residual amount in the separating agent of the separation column for enantiomeric isomers: (506.0−495.6)/4000×100=0.26%

Example 2

(1) Surface Treatment of Carrier (Silica Gel)

The silica gel treated with aminopropylsilane was obtained in the same manner as in Example 1.

(2) Synthesis of Optically Active Polymer Compound

In a nitrogen atmosphere, 10.0 g of amylose was added to 300 ml of pyridine. The resulting mixture was immersed in an oil bath at 100° C., and 50 g of (S)-phenylethylisocyanate was added thereto to conduct a reaction at 100° C. for 48 hours. The reaction liquid was added dropwise to 2 L of methanol, followed by reprecipitation and centrifugal separation, thereby obtaining the objective amylose tris[(S)-phenylethylcarbamate] represented by the following equation.

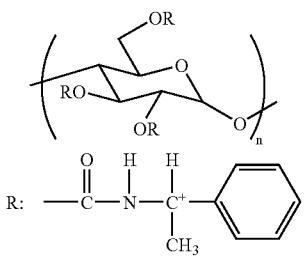

(3) Preparation of Separating Agent for Separating Enantiomeric Isomers 0.8 g of amylose tris[(S)-phenylethylcarbamate] obtained in (2) above and 435.65 mg of (S-1) (2-fold molar equivalent to a glucose unit of amylose tris[(S)-phenylethylcarbamate]) were dissolved in THF to prepare a dope. This dope was applied to 3.2 g of silica gel obtained in (1) above. After the application, THF was distilled off to obtain the objective separating agent for separating enantiomeric isomers. This separating agent was added to a mixed solvent of n-hexane/

2-propanol, and the resulting mixture was well stirred, and filtered. The filtrate was condensed to recover 416.0 mg of (S-1).

(4) Preparation of Packed Column for HPLC

A separation column for enantiomeric isomers was obtained in the same manner as in Example 1.

S-1 residual amount in separating agent for separating enantiomeric isomers: 19.6 mg Elution rate of S-1: 95.5%

S-1 residual amount in separating agent of separation column for enantiomeric isomers: 0.49%

Example 3

(1) Surface Treatment of Carrier (Silica Gel)

The silica gel treated with aminopropylsilane was obtained in the same manner as in Example 1.

(2) Synthesis of Optically Active Polymer Compound

The objective cellulose tris(3,5-dimethylphenylcarbamate) represented by the following formula was obtained in the same manner as in Example 2.

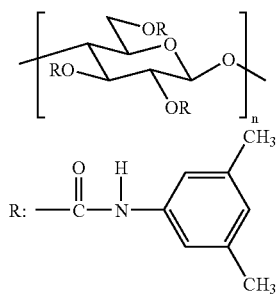

(3) Preparation of Separating Agent for Separating Enantiomeric Isomers 0.8 g of cellulose tris(3,5-dimethylphenylcarbamate) obtained in (2) above and 435.9 mg of (S-1) (2-fold molar equivalent for a glucose unit of cellulose tris(3,5-dimethylphenylcarbamate) were dissolved in acetone to prepare a dope. This dope was applied to 3.2 g of silica gel obtained in (1) above. After the application, acetone was distilled off to obtain the objective separating agent for separating enantiomeric isomers. This separating agent was added to a mixed solvent of n-hexane/2-propanol, and the resulting mixture was well stirred, and filtered. The filtrate was condensed to recover 420.6 mg of (S-1).

(4) Preparation of Packed Column for HPLC

A separation column for enantiomeric isomers was obtained in the same manner as in Example 1.

S-1 residual amount in separating agent for separating enantiomeric isomers: 15.3 mg Elution rate of S-1: 96.5%

S-1 residual amount in separating agent of separation column for enantiomeric isomers: 0.38%

Example 4

(1) Surface Treatment of Carrier (Silica Gel)

The silica gel treated with aminopropylsilane was obtained in the same manner as in Example 1.

(2) Synthesis of Optically Active Polymer Compound

The objective amylose tris(3,5-dimethylphenylcarbamate) represented by the following formula was obtained in the same manner as in Example 2.

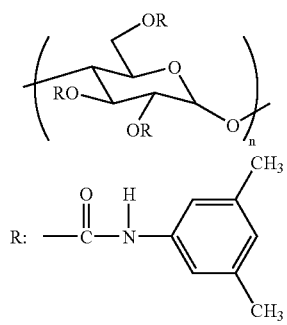

(3) Preparation of Separating Agent for Separating Enantiomeric Isomers 0.8 g of amylose tris(3,5-dimethylphenylcarbamate) obtained in (2) above and 436.3 mg of (S-1) were dissolved in ethyl acetate to prepare a dope. This dope was applied to 3.2 g of silica gel obtained in (1) above. After the application, ethyl acetate was distilled off to obtain the objective separating agent for separating enantiomeric isomers. This separating agent was added to a mixed solvent of n-hexane/2-propanol, and the resulting mixture was well stirred, and filtered. The filtrate was condensed to recover 427.6 mg of (S-1).

(4) Preparation of Packed Column for HPLC

A separation column for enantiomeric isomers was obtained in the same manner as in Example 1.

S-1 residual amount in separating agent for separating enantiomeric isomers: 8.7 mg Elution rate of S-1: 98%

S-1 residual amount in separating agent of separation column for enantiomeric isomers: 0.22%

Examples 5 to 24

Using a compound having an asymmetric structure of a molecular weight of 1,000 or less shown in Table 1, the objective separating agent for separating enantiomeric isomers was obtained by the same production method of each of Examples 1 to 3, and thereafter a separation column for enantiomeric isomers was obtained.

TABLE 1

| Example | Production method (selected from Examples 1 to 3) | Kind of compound having asymmetric structure of molecular weight of 1,000 or less |
| --- | --- | --- |
| 5 | 2 | S-3 |
| 6 | 2 | D-6 |
| 7 | 2 | L-6 |
| 8 | 2 | S-7 |
| 9 | 2 | R-8 |
| 10 | 2 | S-8 |
| 11 | 2 | S-9 |
| 12 | 3 | L-6 |
| 13 | 2 | S-11 |
| 14 | 2 | R-9 |
| 15 | 1 | R-3 |
| 16 | 1 | S-3 |

TABLE 1-continued

| Example | Production method (selected from Examples 1 to 3) | Kind of compound having asymmetric structure of molecular weight of 1,000 or less |
|---|---|---|
| 17 | 1 | D-6 |
| 18 | 1 | R-8 |
| 19 | 1 | Racemi form-13 |
| 20 | 1 | Racemi form-5 |
| 21 | 1 | Racemi form-2 |
| 22 | 1 | Racemi form-14 |
| 23 | 1 | Racemi form-15 |
| 24 | 1 | Racemi form-16 |

Comparative Example 1

The objective separating agent for separating enantiomeric isomers was obtained in the same manner as in Example 1, and thereafter a separation column for enantiomeric isomers was obtained. However, (S-1) was not added.

Comparative Example 2

The objective separating agent for separating enantiomeric isomers was obtained in the same manner as in Example 2, and thereafter a separation column for enantiomeric isomers was obtained. However, (S-1) was not added.

Comparative Example 3

The objective separating agent for separating enantiomeric isomers was obtained in the same manner as in Example 3, and thereafter a separation column for enantiomeric isomers was obtained. However, (S-1) was not added.

Comparative Example 4

The objective separating agent for separating enantiomeric isomers was obtained in the same manner as in Example 4, and thereafter a separation column for enantiomeric isomers was obtained. However, (S-1) was not added.

Application Examples 1 to 45

Using the separation columns for enantiomeric isomers obtained in Examples 1 to 24 and Comparative Examples 1 to 4, α values were measured by liquid chromatography (liquid chromatograph, manufactured by JASCO Co.). The measurement conditions include moving phase: n-hexane/2-propanol=90/10, flow rate: 1.0 ml/min, temperature: 25° C., and detection wavelength: 254 nm. The results are shown in Tables 2 to 4.

The judgement in the tables is judgement of identity, similarity or non-similarity, and the details thereof are described after the tables. An increase rate (%) of a value in the tables was obtained by the following equation: $\alpha_1 - \alpha_2 / \alpha_1 \times 100$. Here, expressed by $\alpha = 1.00$ is the state where asymmetry identification was not conducted at all and only one peak was observed.

TABLE 2

| Application example | Kind of compound having asymmetric structure of molecular weight of 1,000 or less | Compound to be separated Kind | Judgment | Kind of separation column and α value Ex. | $\alpha_1$ | Kind of separation column and α value Com. Ex. | $\alpha_2$ | Increase rate of α value (%) |
|---|---|---|---|---|---|---|---|---|
| 1 | S-1 | Racemi form-1 | Identical | 1 | 1.11 | 1 | 1.00 | 11 |
| 2 | S-1 | Racemi form-1 | Identical | 2 | 4.24 | 2 | 3.73 | 14 |
| 3 | S-1 | Racemi form-1 | Identical | 3 | 1.07 | 3 | 1.00 | 7 |
| 4 | S-1 | Racemi form-2 | Similar | 4 | 1.05 | 4 | 1.00 | 5 |
| 5 | S-3 | Racemi form-4 | Similar | 5 | 2.76 | 2 | 2.32 | 19 |
| 6 | S-3 | Racemi form-5 | Similar | 5 | 3.51 | 2 | 2.45 | 43 |
| 7 | D-6 | Racemi form-5 | Similar | 6 | 3.13 | 2 | 2.45 | 28 |
| 8 | L-6 | Racemi form-4 | Similar | 7 | 2.78 | 2 | 2.32 | 20 |
| 9 | L-6 | Racemi form-5 | Similar | 7 | 3.78 | 2 | 2.45 | 54 |
| 10 | S-7 | Racemi form-2 | Similar | 8 | 1.17 | 2 | 1.00 | 17 |
| 11 | S-7 | Racemi form-5 | Similar | 8 | 3.06 | 2 | 2.45 | 25 |
| 12 | R-8 | Racemi form-2 | Similar | 9 | 1.29 | 2 | 1.00 | 29 |
| 13 | R-8 | Racemi form-4 | Similar | 9 | 2.68 | 2 | 2.32 | 16 |
| 14 | S-8 | Racemi form-2 | Similar | 10 | 1.22 | 2 | 1.00 | 22 |
| 15 | S-8 | Racemi form-5 | Similar | 10 | 3.11 | 2 | 2.45 | 27 |
| 16 | S-9 | Racemi form-4 | Similar | 11 | 2.79 | 2 | 2.32 | 20 |
| 17 | S-9 | Racemi form-5 | Similar | 11 | 2.73 | 2 | 2.45 | 11 |
| 18 | S-1 | Racemi form-2 | Similar | 2 | 1.12 | 2 | 1.00 | 12 |
| 19 | S-1 | Racemi form-5 | Similar | 2 | 2.90 | 2 | 2.45 | 18 |

Application Examples 4 and 18

The compound having the asymmetric structure and the compound to be separated each have an asymmetric carbon atom at the root of a phenyl group. Further, adjacent carbon atoms (β-position) of the asymmetric carbon atoms each have a carbonyl group, and the environment around the asymmetric carbon atoms is similar.

Application Examples 5, 8, 16 and 19

The compound having the asymmetric structure and the compound to be separated each have an asymmetric carbon atom at the root of a hydroxyl group. Further, the environment around the asymmetric carbon atom is similar.

Application Examples 6, 7 and 9

The compound having the asymmetric structure and the compound to be separated each have an asymmetric carbon atom at the root of a hydroxyl group. Further, adjacent carbon atoms ($\alpha$-position) of the asymmetric carbon atoms are each carbonyl groups, and thus, the environment around the asymmetric carbon atoms is similar.

Application Examples 10, 12 and 14

The compound having the asymmetric structure and the compound to be separated each have an asymmetric carbon atom adjacent to an oxygen atom $\alpha$-position). Further, adjacent carbon atoms ($\beta$-position) of the asymmetric carbon atoms each have a carbonyl group, and the environment around the asymmetric carbon atoms is similar.

Application Example 11

The compound having the asymmetric structure and the compound to be separated each have an asymmetric carbon atom adjacent to a carbon atom and have a carbonyl group in a molecule. Thus, the environment around the asymmetric carbon atoms is similar.

Application Example 13

The compound having the asymmetric structure and the compound to be separated each have an asymmetric carbon atom at the root of a trihalogenomethyl substituent. Further, the environment around the asymmetric carbon atom is similar.

Application Examples 15 and 17

The compound having he asymmetric structure and the compound to be separated each have an asymmetric carbon atom adjacent to an oxygen atom ($\alpha$-position) and have a carbonyl group in the vicinity of the asymmetric carbon atoms, and the environment around the asymmetric carbon atoms is similar.

TABLE 2

| Application example | Kind of compound having asymmetric structure of molecular weight of 1,000 or less | Compound to be separated | | Kind of separation column and $\alpha$ value | | Kind of separation column and $\alpha$ value | | Increase rate of $\alpha$ value (%) |
|---|---|---|---|---|---|---|---|---|
| | | Kind | Judgment | Ex. | $\alpha_1$ | Com. Ex. | $\alpha_2$ | |
| 1 | S-1 | Racemi form-1 | Identical | 1 | 1.11 | 1 | 1.00 | 11 |
| 2 | S-1 | Racemi form-1 | Identical | 2 | 4.24 | 2 | 3.73 | 14 |
| 3 | S-1 | Racemi form-1 | Identical | 3 | 1.07 | 3 | 1.00 | 7 |
| 4 | S-1 | Racemi form-2 | Similar | 4 | 1.05 | 4 | 1.00 | 5 |
| 5 | S-3 | Racemi form-4 | Similar | 5 | 2.76 | 2 | 2.32 | 19 |
| 6 | S-3 | Racemi form-5 | Similar | 5 | 3.51 | 2 | 2.45 | 43 |
| 7 | D-6 | Racemi form-5 | Similar | 6 | 3.13 | 2 | 2.45 | 28 |
| 8 | L-6 | Racemi form-4 | Similar | 7 | 2.78 | 2 | 2.32 | 20 |
| 9 | L-6 | Racemi form-5 | Similar | 7 | 3.78 | 2 | 2.45 | 54 |
| 10 | S-7 | Racemi form-2 | Similar | 8 | 1.17 | 2 | 1.00 | 17 |
| 11 | S-7 | Racemi form-5 | Similar | 8 | 3.06 | 2 | 2.45 | 25 |
| 12 | R-8 | Racemi form-2 | Similar | 9 | 1.29 | 2 | 1.00 | 29 |
| 13 | R-8 | Racemi form-4 | Similar | 9 | 2.68 | 2 | 2.32 | 16 |
| 14 | S-8 | Racemi form-2 | Similar | 10 | 1.22 | 2 | 1.00 | 22 |
| 15 | S-8 | Racemi form-5 | Similar | 10 | 3.11 | 2 | 2.45 | 27 |
| 16 | S-9 | Racemi form-4 | Similar | 11 | 2.79 | 2 | 2.32 | 20 |
| 17 | S-9 | Racemi form-5 | Similar | 11 | 2.73 | 2 | 2.45 | 11 |
| 18 | S-1 | Racemi form-2 | Similar | 2 | 1.12 | 2 | 1.00 | 12 |
| 19 | S-1 | Racemi form-5 | Similar | 2 | 2.90 | 2 | 2.45 | 18 |

TABLE 4

| Application example | Kind of compound having asymmetric structure of molecular weight of 1,000 or less | Compound to be separated | | Kind of separation column and $\alpha$ value | | Kind of separation column and $\alpha$ value | | Increase rate of $\alpha$ value (%) |
|---|---|---|---|---|---|---|---|---|
| | | Kind | Judgment | Ex. | $\alpha_1$ | Com. Ex. | $\alpha_2$ | |
| 39 | Racemi form-13 | Racemi form-13 | Identical | 19 | 1.82 | 1 | 1.67 | 9 |
| 40 | Racemi form-14 | Racemi form-14 | Similar | 19 | 1.61 | 1 | 1.35 | 19 |
| 41 | Racemi form-5 | Racemi form-12 | Non-similar | 20 | 1.41 | 1 | 1.22 | 16 |
| 42 | Racemi form-2 | Racemi form-12 | Non-similar | 21 | 1.52 | 1 | 1.22 | 25 |
| 43 | Racemi form-14 | Racemi form-12 | Non-similar | 22 | 1.48 | 1 | 1.22 | 21 |
| 44 | Racemi form-15 | Racemi form-12 | Non-similar | 23 | 1.46 | 1 | 1.22 | 20 |
| 45 | Racemi form-16 | Racemi form-12 | Non-similar | 23 | 1.43 | 1 | 1.22 | 17 |

Application Example 40

The compound having the asymmetric structure and the compound to be separated each have an asymmetric carbon atom at the root of a hydroxyl group, and the structure of the molecule as a whole includes a condensed ring similar to a naphthyl group and an anthranyl group. Therefore, the environment around the asymmetric carbon atom is similar.

The invention claimed is:

1. A method of producing a novel separating agent for separating enantiomeric isomers, comprising: a step of supporting an optically active polymer compound and a compound having an asymmetric structure of a molecular weight of 1,000 or less on a carrier using a solvent added as a production raw material; a step of removing the solvent; and a step of removing the compound having the asymmetric structure of the molecular weight of 1,000 or less by washing to form the separating agent having enhanced asymmetric identification ability.

2. The method of producing a novel separating agent for separating enantiomeric isomers as claimed in claim 1, wherein supporting the optically active polymer compound on the carrier is conducted by physical adsorption.

3. The method of producing a novel separating agent for separating enantiomeric isomers as claimed in claim 1, wherein supporting the optically active polymer compound on the carrier is conducted by chemical bonding.

4. The method of producing a novel separating agent for separating enantiomeric isomers as claimed in claim 3, wherein the carrier and the optically active polymer compound are chemically bonded before or after the removal of the compound having the asymmetric structure of the molecular weight of 1,000 or less.

5. The method of producing a novel separating agent for separating enantiomeric isomers as claimed in claim 3, wherein the carrier and the optically active polymer compound are chemically bonded by a reaction with a crosslinking agent, a reaction with a radical generator or irradiation with light before or after the removal of the compound having the asymmetric structure of the molecular weight of 1,000 or less.

6. The method of producing a novel separating agent for separating enantiomeric isomers as claimed in claim 1, wherein the optically active polymer compound has an asymmetry identification ability to a compound to be separated when used as the separating agent for separating the enantiomeric isomers.

7. The method of producing a novel separating agent for separating enantiomeric isomers as claimed in claim 1, wherein the optically active polymer compound is a polysaccharide derivative.

8. The method of producing a novel separating agent for separating enantiomeric isomers as claimed in claim 1, wherein the optically active polymer compound is a polysaccharide ester derivative or carbamate derivative.

9. The method of producing a novel separating agent for separating enantiomeric isomers as claimed in claim 1, wherein the optically active polymer compound is a cellulose derivative or an amylose derivative.

10. The method of producing a novel separating agent for separating enantiomeric isomers as claimed in claim 1, wherein the optically active polymer compound is a polymer or a copolymer of acrylamides, methacrylamides, acrylates or methacrylates having an optically active substituents on a side chain.

11. The method of producing a novel separating agent for separating enantiomeric isomers as claimed in claim 1, wherein an amount of the optically active polymer compound supported on the carrier is 1 to 100 mass % to a mass of the carrier.

12. The method of producing a novel separating agent for separating enantiomeric isomers as claimed in claim 1, wherein the compound having the asymmetric structure of the molecular weight of 1,000 or less is a compound to be separated or a similarly structured compound thereof when used as the separating agent for separating the enantiomeric isomers.

13. The method of producing a novel separating agent for separating enantiomeric isomers as claimed in claim 1, wherein the compound having the asymmetric structure of the molecular weight of 1,000 or less is not a compound to be separated or a similarly structured compound thereof when used as the separating agent for separating the enantiomeric isomers.

14. The method of producing a novel separating agent for separating enantiomeric isomers as claimed in claim 13, wherein the compound having the asymmetric structure of the molecular weight of 1,000 or less is not the compound to be separated or the similarly structured compound thereof when used as the separating agent for separating the enantiomeric isomers, and is a compound having a cyclic structure of a molecular weight of 40 to 1000.

15. The method of producing a novel separating agent for separating enantiomeric isomers as claimed in claim 1, wherein the compound having the asymmetric structure of the molecular weight of 1,000 or less is a racemi form and/or an optically active substance.

16. The method of producing a novel separating agent for separating enantiomeric isomers as claimed in claim 1, wherein the amount of the compound having the asymmetric structure of the molecular weight of 1,000 or less supported on the carrier is 0.01 to 1,000 mass % to a mass of the optically active polymer compound.

17. The method of producing a novel separating agent for separating enantiomeric isomers as claimed in claim 1, wherein a residual amount of the compound having the asymmetric structure of the molecular weight of 1,000 or less is 10 mass % or less in the separating agent for separating the enantiomeric isomers.

18. The method of producing a novel separating agent for separating enantiomeric isomers as claimed claim 1, wherein the compound having the asymmetric structure of the molecular weight of 1,000 or less is substantially removed.

19. The method of producing a novel separating agent for separating enantiomeric isomers as claimed in claim 1, wherein the compound having the asymmetric structure of the molecular weight of 1,000 or less is the compound to be separated or the similarly structured compound thereof when used as the separating agent for separating the enantiomeric isomers, and when the enantiomeric isomers are separated using the obtained separating agent for separating the enantiomeric isomers, a separation performance based on a separation coefficient ($\alpha$) obtained by the following equation:

separation coefficient ($\alpha$)=(holding coefficient of enantiomer held relatively strongly)/(holding coefficient of the enantiomer held relatively weakly)

holding coefficient ($k'$)=[(holding time of the enantiomer)−(dead time)]/(dead time)

is represented by the following equation (A) or equation (B):

$$\alpha_1/\alpha_2 \geq 1.05, \text{ provided } \alpha_2=1.00 \quad (A)$$

$$\alpha_1/\alpha_2 \geq 1.05, \text{ provided } \alpha_2>1.00 \quad (B)$$

where $\alpha_1$: a separation coefficient of the separating agent for separating the enantiomeric isomers obtained by adding the compound having the asymmetric structure of the molecular weight of 1,000 or less in a production step, and $\alpha_2$: a separation coefficient of the separating agent for separating the enantiomeric isomers obtained without adding the compound having the asymmetric structure of the molecular weight of 1,000 or less in the production step, in which $\alpha_2 2=1.00$ means that the enantiomeric isomers are not separated al all, and $\alpha_2>1.00$ means that the enantiomeric isomers are separated.

20. The method of producing a novel separating agent for separating enantiomeric isomers as claimed in claim 1,
wherein the compound having the asymmetric structure of the molecular weight of 1,000 or less is not the compound to be separated or the similarly structured compound thereof when used as the separating agent for separating the enantiomeric isomers, and when the enantiomeric isomers are separated using the obtained separating agent for separating the enantiomeric isomers, a separation performance based on a separation coefficient ($\alpha$) obtained by the following equation:

separation coefficient ($\alpha$)=(holding coefficient of enantiomer held relatively strongly)/(holding coefficient of the enantiomer held relatively weakly)

holding coefficient ($k'$)=[(holding time of the enantiomer)−(dead time)]/(dead time)

is represented by the following equation (A) or equation (B):

$$\alpha_1/\alpha_2 \geq 1.05, \text{ provided } \alpha_2=1.00 \quad (A)$$

$$\alpha_1/\alpha_2 \geq 1.05, \text{ provided } \alpha_2>1.00 \quad (B)$$

where $\alpha_1$: a separation coefficient of the separating agent for separating the enantiomeric isomers obtained by adding the compound having the asymmetric structure of the molecular weight of 1,000 or less in a production step, and $\alpha_2$: a separation coefficient of the separating agent for separating the enantiomeric isomers obtained without adding the compound having the asymmetric structure of the molecular weight of 1,000 or less in the production step, in which $\alpha_2=1.00$ means that the enantiomeric isomers are not separated al all, and $\alpha_2>1.00$ means that the enantiomeric isomers are separated.

21. The method of producing a novel separating agent for separating enantiomeric isomers as claimed in claim 20, wherein the compound having the asymmetric structure of the molecular weight of 1,000 or less is not the compound to be separated or the similarly structured compound thereof when used as the separating agent for separating the enantiomeric isomers, and is a compound having a cyclic structure of a molecular weight of 40 to 1000.

22. The method of producing a novel separating agent for separating enantiomeric isomers as claimed in claim 1, wherein the residual amount of the compound having the asymmetric structure of the molecular weight of 1,000 or less is 0.5 mass % or less in the separating agent.

23. The method of producing a novel separating agent for separating enantiomeric isomers as claimed in claim 1, wherein the compound having the asymmetric structure of the molecular weight of 1,000 or less is a member selected from the group consisting of 1-phenyl-2-propanol, 1-phenylethanol, 2-phenyl-2-propanol, 1-phenyl-2-butanol, 2-phenyl-2-butanol, 3-phenyl-2-butanol, 1-substituted phenyl-2-propanol, 1-(1-naphthyl)-2-propanol, 1-(2-pyridyl)-2-propanol, 1-cyclohexyl-2-propanol, 1-(1-naphthyl)-ethanol and 1-(9-anthryl)-ethanol.

24. The method of producing a novel separating agent for separating enantiomeric isomers as claimed in claim 1, wherein the compound having the asymmetric structure of the molecular weight of 1,000 or less is a member selected from the group consisting of

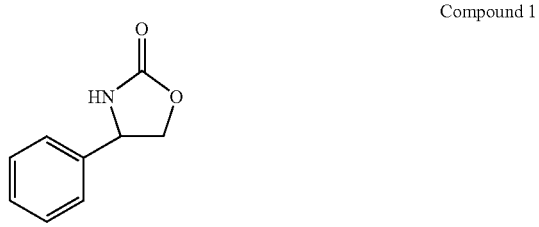

Compound 1

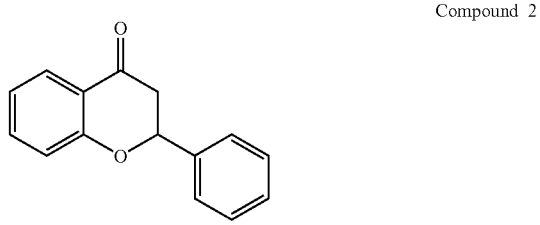

Compound 2

Compound 3

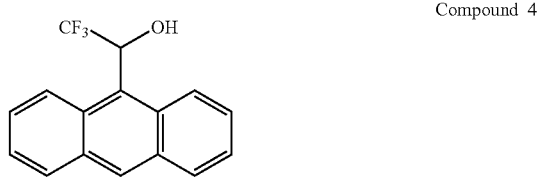

Compound 4

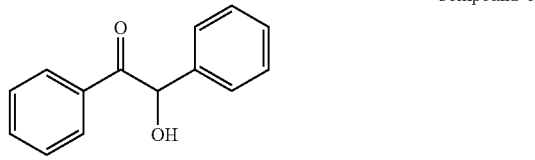

Compound 5

Compound 6

25. The method of producing a novel separating agent for separating enantiomeric isomers as claimed in claim 1, wherein the optically active polymer compound contains monomer units selected from the group consisting of cellulose tris(4-methylbenzoate), amylos tris[(S)-phenylethylcarbamate], cellulose tris(3,5-dimethylphenylcarbamate) and amylos tris(3,5-dimethylphenylcarbamate).

26. A method of producing a novel separating agent for separating enantiomeric isomers, comprising: a step of supporting an optically active polymer compound on a carrier using a solvent added as a production raw material; a step of additionally supporting a compound having an asymmetric structure of a molecular weight of 1,000 or less on the carrier; a step of removing the solvent; and a step of removing the compound having the asymmetric structure of the molecular weight of 1,000 or less by washing to form the separating agent having enhanced asymmetric identification ability.

27. The method of producing a novel separating agent for separating enantiomeric isomers as claimed in claim 26, wherein the residual amount of the compound having the asymmetric structure of the molecular weight of 1,000 or less is 0.5 mass % or less in the separating agent.

28. The method of producing a novel separating agent for separating enantiomeric isomers as claimed in claim 26, wherein the compound having the asymmetric structure of the molecular weight of 1,000 or less is a member selected from the group consisting of 1-phenyl-2-propanol, 1-phenylethanol, 2-phenyl-2-propanol, 1-phenyl-2-butanol, 2-phenyl-2-butanol, 3-phenyl-2-butanol, 1-substituted phenyl-2-propanol, 1-(1-naphthyl)-2-propanol, 1-(2-pyridyl)-2-propanol, 1-cyclohexyl-2-propanol, 1-(1-naphthyl)-ethanol and 1-(9-anthryl)-ethanol.

29. The method of producing a novel separating agent for separating enantiomeric isomers as claimed in claim 26, -continued

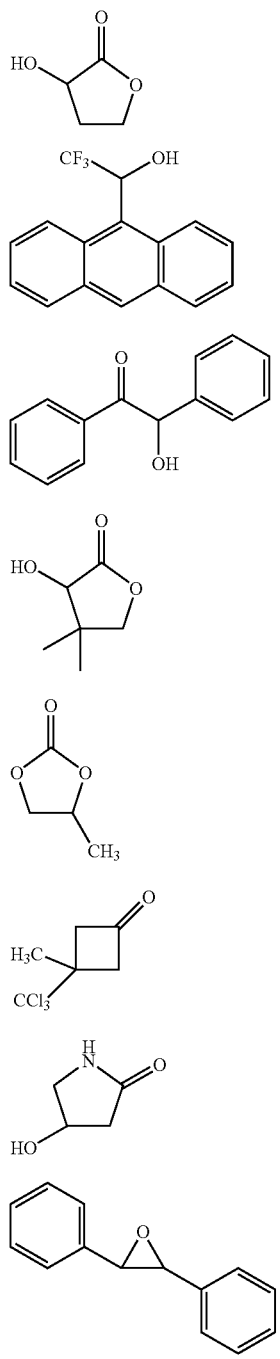

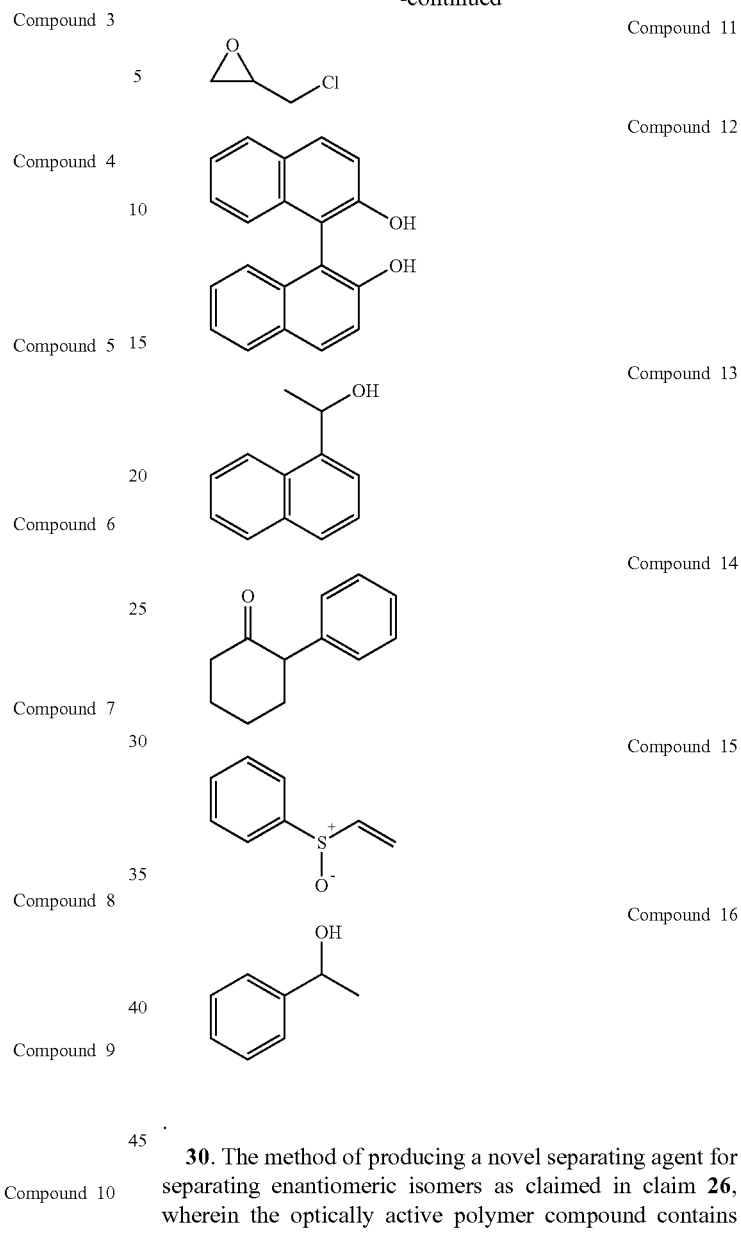

30. The method of producing a novel separating agent for separating enantiomeric isomers as claimed in claim 26, wherein the optically active polymer compound contains monomer units selected from the group consisting of cellulose tris(4-methylbenzoate), amylos tris[(S)-phenylethylcarbamate], cellulose tris(3,5-dimethylphenylcarbamate) and amylos tris(3,5-dimethylphenylcarbamate).

* * * * *